United States Patent [19]

Büchel et al.

[11] 4,159,342
[45] Jun. 26, 1979

[54] SUBSTITUTED 2-ACYLOXYBENZOIC ACID ANILIDES

[75] Inventors: Karl H. Büchel, Wuppertal-Elberfeld; Ingeborg Hammann, Cologne, both of Fed. Rep. of Germany

[73] Assignee: Bayer Aktiengesellschaft, Leverkusen, Fed. Rep. of Germany

[21] Appl. No.: 836,989

[22] Filed: Sep. 27, 1977

Related U.S. Application Data

[60] Continuation of Ser. No. 574,125, May 2, 1975, abandoned, which is a division of Ser. No. 246,011, Apr. 20, 1972, Pat. No. 3,906,023.

[30] Foreign Application Priority Data

Apr. 28, 1971 [DE] Fed. Rep. of Germany ....... 2120862

[51] Int. Cl.² .................. C07C 69/14; C07C 69/34; A01N 9/24
[52] U.S. Cl. ...................................... 424/311; 560/138
[58] Field of Search ...................... 560/138; 424/311

[56] References Cited
U.S. PATENT DOCUMENTS

| | | | |
|---|---|---|---|
| 3,079,297 | 2/1963 | Schaufstatter et al. | 424/230 |
| 3,469,006 | 9/1969 | Ehrouford et al. | 424/230 |
| 3,519,678 | 7/1970 | Farrington | 560/138 |
| 3,823,236 | 7/1974 | Buchel et al. | 424/230 |

Primary Examiner—Robert Gerstl
Attorney, Agent, or Firm—Sprung, Felfe, Horn, Lynch & Kramer

[57] ABSTRACT

Substituted 2-acyloxybenzoic acid anilides of the general formula

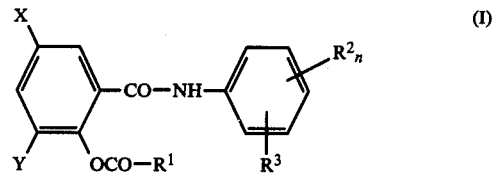

in which
R¹ is alkyl or alkoxy with up to 6 carbon atoms,
R² is lower alkyl, halo-lower alkyl, halo, nitro, lower alkyoxycarbonyloxy or lower acyloxy,
R³ is hydrogen, lower alkyl, halo-lower alkyl, lower alkoxy, lower alkylmercapto, halo, nitro or lower alkoxycarbonyloxy,
n is 1, 2 or 3, and
X is hydrogen and Y is nitro, or
X is bromine or tertiary butyl and Y is chlorine or bromine, or
X is chlorine and Y is chlorine or bromine, or hydrogen with R¹ being alkoxy, which possess insecticidal and acaricidal properties.

4 Claims, No Drawings

SUBSTITUTED 2-ACYLOXYBENZOIC ACID ANILIDES

This is a continuation of application Ser. No. 574,125, filed May 2, 1975, now abandoned, which was a division of application Ser. No. 246,011 filed Apr. 20, 1972, now U.S. Pat. No. 3,906,023, issued Sept. 16, 1975.

The present invention relates to and has for its objects the provision of particular new substituted 2-acyloxybenzoic acid anilides, i.e. 2-acyloxybenzoic acid anilides substituted in the 3-position and in some instances in the 5-position as well as being substituted at least once on the aniline ring, which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. No. 3,079,297 and Zeitschrift für Naturforschung 16 b, 95 (1961) that derivatives of 2-hydroxybenzoic acid anilides are effective against gastropods as well as molluscs.

It is furthermore known from U.S. Pat. Nos. 3,216,896; 3,249,637; 3,454,638 and 3,525,766 and German Published Specifications DAS Nos. 1,300,926 and 1,542,944 that 3,5-disubstituted 2-hydroxybenzoic acid anilides possess an insecticidal and acaricidal effectiveness, for example 5,4'-dichloro-2-hydroxy-3-p-chlorophenylbenzoic acid anilide (Compound A) and 5,2',4',5'-tetrachloro-2-hydroxy-3-p-chlorophenyl-benzoic acid anilide (Compound B). The effectiveness of these compounds, in particular against many Tetranychus and Plutella species, is, however, not always wholly satisfactory especially in the case of low application concentrations.

The present invention provides 2-acyloxybenzoic acid anilides of the general formula:

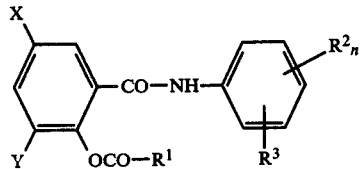

(I)

in which
R$^1$ is alkyl or alkoxy with up to 6 carbon atoms,
R$^2$ is lower alkyl, halo-lower alkyl, halo, nitro, lower alkyoxycarbonyloxy or lower acyloxy,
R$^3$ is hydrogen, lower alkyl, halo-lower alkyl, lower alkoxy, lower alkylmercapto, halo, nitro or lower alkoxycarbonyloxy,
n is 1, 2 or 3, and
X is hydrogen and Y is nitro, or
X is bromine or tertiary butyl and Y is chlorine or bromine, or
X is chlorine and Y is chlorine or bromine, or hydrogen with R$^1$ being alkoxy,
which exhibit insecticidal and acaricidal properties.

Preferably R$^1$ is lower alkyl or alkoxy with up to 4 carbon atoms: R$^2$ is alkyl with up to 4, especially up to 3, carbon atoms, trihalomethyl, chlorine, bromine, nitro, ethoxycarbonyloxy or acyloxy with an alkyl moiety containing up to 4, especially up to 3, carbon atoms; and R$^3$ is straight and branched alkyl, alkoxy or alkylmercapto with up to 4, especially up to 3, carbon atoms, trihalomethyl, chlorine, bromine, nitro or ethoxycarbonyloxy.

The invention also provides a process for the production of a 2-acyloxybenzoic acid anilide of the formula (I) in which a 3,5-disubstituted 2-hydroxybenzoic acid anilide or salt thereof, known in the art, of the general formula:

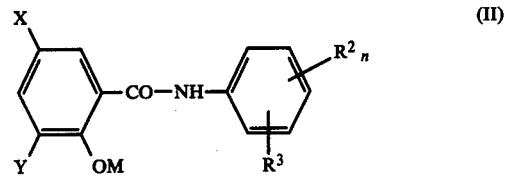

(II)

in which
X, Y, R$^2$, R$^3$ and n have the meanings stated above, and
M is hydrogen or an equivalent amount of a cation especially an alkali metal,
is reacted with an acid chloride of the formula:

$$R^1\text{—CO—Cl}$$ (III)

in which R$^1$ has the meaning stated above,
optionally in the presence of an acid-binder and optionally in the presence of a diluent.

Surprisingly, the 2-acyloxybenzoic acid anilides according to the invention show a considerably higher insecticidal and acaricidal activity than the 4,5'-dichloro-2-hydroxy-3-p-chlorophenyl-benzoic acid anilide and 5,2',4',5'-tetrachloro-2-hydroxy-3-p-chlorophenyl-benzoic acid anilide known from the prior art which are the chemically closest active compounds of the same type of activity. The substances according to the invention therefore represent an enrichment of the art.

If 3-bromo-5-chloro-3',5'-bistrifluoromethyl-2-hydroxy-benzoic acid anilide and chloroformic acid methyl ester are used as starting materials, the reaction course can be represented by the following formula scheme:

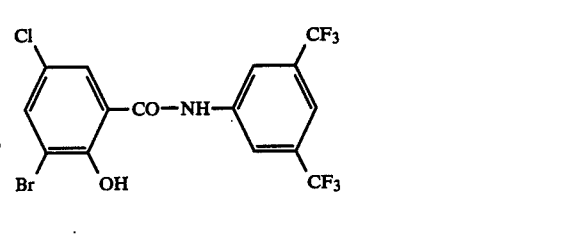

(IIa)

$$\text{Cl—CO—OCH}_3 \xrightarrow{\text{acid binder}}$$

(IIIa)

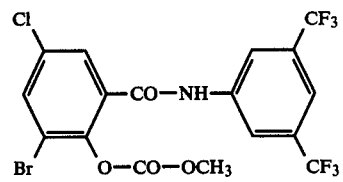

(IV)

When M is hydrogen the reaction is preferably carried out in the presence of inert, especially slightly polar, organic solvents or diluents. These include preferably hydrocarbons such as benzene, toluene or xylene; ethers such as diethyl ether and dibutyl ether; chlorinated hydrocarbons such as chloroforom or carbon tetrachloride. The reaction of the salts takes place preferably in the presence of polar organic solvents or diluents such as ketones, e.g. acetone; ethers such as dioxane; alcohols such as methanol; nitriles such as acetonitrile; and the like.

As acid-binders, all customary acid-binding agents can be used. Particularly suitable are alkali metal hydroxides, such as potassium hydroxide or sodium hydroxide, alkali metal carbonates, such as sodium carbonate or potassium carbonate, alkaline earth metal carbonates, such as barium carbonate, and tertiary organic bases, such as trimethylamine or pyridine.

The carrying out of the process according to the invention is possible within a fairly wide temperature range. In general, the work is carried out at about 0° C. to 120° C., preferably about 10° C. to 100° C.

When carrying out the process according to the invention, for each mole of the compound of the formula (II) there are used between about 1.2 and 1.5 moles of the compound of the formula (III) and, where appropriate, the equivalent amount of acid-binder. A further exceeding of the stoichiometric proportions brings no substantial improvement of yield. For isolation, filtration from the chloride formed is effected hot, the solvent is distilled off in a vacuum and the products concerned are purified by recrystallization.

As examples of the products according to the invention, there are mentioned in particular:

3,5-dibromo-3',5'-bistrifluoromethyl-2-methoxycarbonyloxybenzoic acid anilide,
3-bromo-5,2'-dichloro-5-trifluoromethyl-2-propionyloxybenzoic acid anilide,
3,5-dibromo-2',6'-diisopropyl-2-acetoxy-benzoic acid anilide,
3,5-dibromo-2',6'-diisopropyl-2-priopionyloxy-benzoic acid anilide,
3,5-dichloro-2',6'-diisopropyl-2-propionyloxy-benzoic acid anilide,
3-bromo-5-chloro-3',5'-bistrifluoromethyl-2-acetoxybenzoic acid anilide,
3-bromo-5-chloro-3',5'-bistrifluoromethyl-2-propionyloxybenzoic acid anilide,
3-bromo-5,2'-dichloro-5'-trifluoromethyl-2-methoxycarbonyloxybenzoic acid anilide,
3-bromo-5,2'-dichloro-5'-trifluoromethyl-2-acetoxybenzoic acid anilide,
3,5-dibromo-2'-chloro-5'-trifluoromethyl-2-methoxycarbonyloxybenzoic acid anilide,
3,5,2'-trichloro-5'-trifluoromethyl-2-propionyloxybenzoic acid anilide,
3,5-dibromo-2',6'-dimethyl-2-methoxycarbonyloxybenzoic acid anilide,
3-bromo-5-chloro-2',6'-diethyl-2-ethoxycarbonyloxybenzoic acid anilide,
3,2',4',6'-tetrabromo-5-tertiary-butyl-2-methoxycarbonyloxybenzoic acid anilide,
3,5-dichloro-2',4',6'-tribromo-2-methoxycarbonyloxy-benzoic acid anilide,
3,3', 5-trichloro-2-ethoxycarbonyloxy-benzoic acid anilide,
3,4',5-trichloro-2-ethoxycarbonyloxy-benzoic acid anilide,
3,3',5,5'-tetrachloro-4'-methylthio-2-ethoxycarbonyloxybenzoic acid anilide,
3,4',5-tribromo-2-ethoxycarbonyloxy-benzoic acid anilide,
3,5-dibromo-2',3'-dichloro-2-ethoxycarbonyloxy-benzoic acid anilide,
4'-chloro-3-nitro-2-ethoxycarbonyloxy-benzoic acid anilide,
2',3,3',5,5'-pentachloro-2,6'-bisethoxycarbonyloxy-benzoic acid anilide,
3,5-dibromo-2',4'-dichloro-2-butoxycarbonyloxy-benzoic acid anilide,
3,5-dibromo-2',4'-dichloro-2-isobutoxycarbonyloxy-benzoic acid anilide, and
2',4',6'-tribromo-3,5-dichloro-2-isobutoxycarbonyloxybenzoic acid anilide.

The 2-acyloxybenzoic acid anilides according to the invention possess an outstanding, rapidly commencing and long-lasting insecticidal and acaricidal effectiveness. They are used with success in crop protection for the control of noxious sucking and biting insects and harmful mites.

To the sucking insects contemplated herein there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina) for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*; and the like.

In the case of the biting insects contemplated herein, above all there should be mentioned butterfly caterpillars (Lepidoptera) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*); and the like.

With the mites (Acari) contemplated herein there are classed, in particular, the spider mites (Tetranychidae) such as the two-spotted spider mite (*Tetranychus telarius=Tetranychus althaeae* or *Tetranychus urticae*) and the European red mite (*Paratetranychus pilosus=Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*).

Particularly worthy of mention is the excellent effectiveness of the active compounds according to the invention against resistant strains of mites, for example against resistant Tetranychus species, as well as against soil insects and insect larvae.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylenes, alkyl naphthalenes, etc.), halogenated, especially chlorinated, aromatic hydrocarbons (e.g. chlorobenzenes, etc.), paraffins (e.g. petroleum and mineral oil fractions), cyclohexane, chlorinated aliphatic hydrocarbons (e.g. methylene chloride, chloroethylenes, etc.), alcohols (e.g. methanol, ethanol, propanol, butanol, glycol, etc.), ethers and esters of such alcohols (e.g. glycol monomethyl ether, etc.), amines (e.g. ethanolamine, etc.), amides (e.g. dimethyl formamide, etc.), sulfoxides (e.g. dimethyl sulfoxide, etc.), ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, egg. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, etc., and especially alkyl arylpolyglycol ethers, magnesium stearate, sodium oleate, etc.); and/or dispersing atents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or fungicides, bactericides, nematocides, rodenticides, herbicides, fertilizers, growth-regulating agents, etc., if desired, or in the form of particular dosage preparations for specific application made therefrom, such as solutions, emulsions, supensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, (c) the corresponding habitat thereof, i.e. the locus to be protected, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The preparation and unexpected superiority and outstanding activity of the particular new compounds of the present invention are illustrated, without limitation, by the following examples:

EXAMPLE 1

(a) Preparation of the starting product:

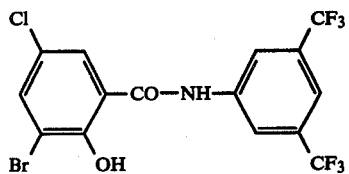

52 g (0.22 mole) of 5-chloro-3-bromosalicylic acid chloride and 62 g (0.27 mole) of 3,5-bistrifluoromethylaniline in 800 ml of anhydrous xylene are heated under reflux for 6 hours. The still hot solution is filtered. The precipitate formed during cooling is filtered off with suction and washed with petroleum ether. 78 g (87.5% of theory) of 3-bromo-5-chloro-3',5'-bis-trifluoromethyl-2-hydroxy-benzoic acid anilide are obtained as slightly yellow crystals of the melting point 167° C.

(b) To a solution of 20 g (0.043 mole) of 3-bromo-5-chloro-3',5'-bistrifluoromethyl-2-hydroxy-benzoic acid anilide in 400 ml of anhydrous benzene there are added 3.5 g (0.04 mole) of pyridine. Thereafter, a solution of 6.2 g (0.065 mole) of chloroformic acid methyl ester in 50 ml of anhydrous benzene is slowly added dropwise at a temperature of 20° to 28° C. The reaction mixture, after sixteen hours heating to 35° C., is cooled to room temperature and the solvent is distilled off in a vacuum. The oily residue obtained is rubbed with methanol. A solid substance forms which is recrystallized from 300 ml of methanol. 12 g (54% of theory) of 3-bromo-5-chloro-3',5'-bis-trifluoromethyl-2-methyoxycarbonyloxy-benzoic acid anilide are obtained as colorless crystals of the melting point 132°–133° C. and the formula

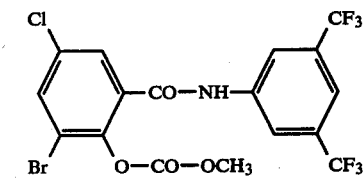

EXAMPLE 2

(a) Preparation of the starting product:

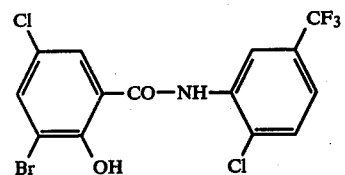

54 g (0.2 mole) of 3-bromo-5-chloro-2-hydroxybenzoic acid chloride and 53 g (0.27 mole) of 4-chloro-3-amino-benzoic trifluoride are heated to the boil for 6 hours in 800 ml of anhydrous xylene. After filtration of the still hot solution, it is left to stand to cool. Pale yellow crystal of 3-bromo-2',5-dichloro-2-hydroxy-5'-trifluoromethyl-benzoic acid anilide, which are well washed with petroleum ether, are obtained in a yield of 65.7 g (83% of theory) with the melting point 154°–156° C.

(b) To a solution of 20 g (0.046 mole) of the product of (a) in 400 ml of anhydrous benzene there are added 3.7 g (0.046 mole) of pyridine, and a solution of 4.5 g (0.05 mole) of propionyl chloride in 50 ml of benzene is slowly added dropwise at temperatures between 20° C. and 30° C. After a reaction time of 16 hours at 35° C., filtration from the pyridine hydrochloride also formed is effected hot and the residue is recrystallized from ligroin. There are obtained 18.5 g (82% of theory) of 3-bromo-2',5-dichloro-5'-trifluoromethyl-2-propionoxy-benzoic acid anilide of the melting point 117° C. and the formula

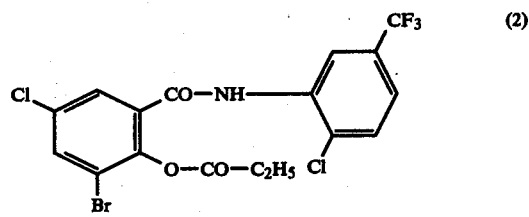

EXAMPLE 3

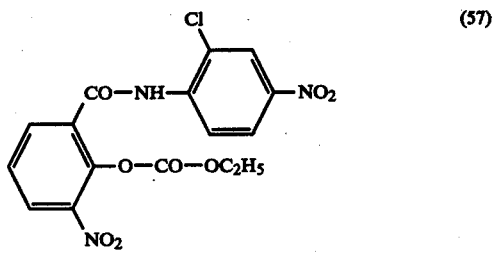

First, a sodium ethylate solution of 2.3 g (0.1 mole) of sodium in 200 ml of anhydrous ethanol is added to a suspension of 33.7 g (0.108 mole) of 2'-chloro-2-hydroxy-3,4'-dinitro-benzoic acid anilide in 350 ml of anhydrous acetonitrile. Thereafter, 11.9 g (0.15 mole) of chloroformic acid ethyl ester in 50 ml of anhydrous acetonitrile are added dropwise. After a reaction time of 24 hours, centrifuging off from the sodium chloride formed is effected, the solvent is distilled off in a vacuum and the oily residue is washed with methanol. 15 g (34% of theory) of 2'-chloro-3,4'-dinitro-2-ethoxycarbonyloxybenzoic acid anilide of the melting point 146°–150° C. are obtained.

EXAMPLES 4–57

The following compounds are prepared in a manner analogous to that of the above Examples 1–3.

Table 1

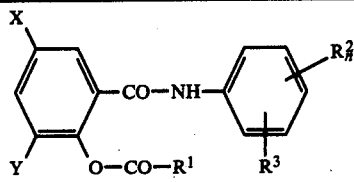

| Example Number | X | Y | R¹ | R² | n | R³ | Melting point °C. |
|---|---|---|---|---|---|---|---|
| 4 | Br | Br | $CH_3$ | 2',6'-$CH(CH_3)_2$ | 2 | H | 167 |
| 5 | Br | Br | $C_2H_5$ | 2',6'-$CH(CH_3)_2$ | 2 | H | 156 |
| 6 | Cl | Cl | $C_2H_5$ | 2',6'-$CH(CH_3)_2$ | 2 | H | 155 |
| 7 | Cl | Br | $CH_3$ | 3',5'-$CF_3$ | 2 | H | 170–71 |
| 8 | Cl | Br | $C_2H_5$ | 3',5'-$CF_3$ | 2 | H | 146–48 |
| 9 | Cl | Br | $OCH_3$ | 2'-Cl | 1 | 5'-$CF_3$ | 134–35 |
| 10 | Cl | Br | $CH_3$ | 2'-Cl | 1 | 5'-$CF_3$ | 155 |
| 11 | Br | Br | $OCH_3$ | 3',5'-$CF_3$ | 2 | H | 145–47 |
| 12 | Br | Br | $OCH_3$ | 2'-Cl | 1 | 5'-$CF_3$ | 132–34 |
| 13 | Cl | Cl | $C_2H_5$ | 2'-Cl | 1 | 5'-$CF_3$ | 93 |
| 14 | Br | Br | $OCH_3$ | 2',6'-$CH_3$ | 2 | H | 161 |
| 15 | Cl | Br | $OCH_3$ | 2',6'-$C_2H_5$ | 2 | H | 146 |
| 16 | $C(CH_3)_3$ | Br | $OCH_3$ | 2',4',6'-Br | 3 | H | 183 |
| 17 | Cl | Cl | $OCH_3$ | 2',4',6'-Br | 3 | H | 175 |
| 18 | Cl | Cl | $OC_2H_5$ | 3'-Cl | 1 | H | 125–29 |
| 19 | Cl | Cl | $OC_2H_5$ | 4'-Cl | 1 | H | 148 |
| 20 | Cl | Cl | $OC_2H_5$ | 2',4',5'-Cl | 3 | H | 142–44 |
| 21 | Cl | Cl | $OC_2H_5$ | 3',5'-Cl | 2 | 4'-$SCH_3$ | 140–43 |
| 22 | Br | Br | $OC_2H_5$ | 4'-Br | 1 | H | 179 |
| 23 | Br | Br | $OC_2H_5$ | 2',3'-Cl | 2 | H | 130 |
| 24 | H | $NO_2$ | $OC_2H_5$ | 4'-Cl | 1 | H | 133 |
| 25 | Cl | Cl | $OC_2H_5$ | 2',3',5'-Cl | 3 | 6'-O—CO—$OC_2H_5$ | 163–65 |
| 26 | Br | Br | $OC_4H_9$ | 2',4'-Cl | 2 | H | 99–101 |
| 27 | Br | Br | $OCH_2$—$CH(CH_3)$—$CH_3$ | 2',4'-Cl | 2 | H | 152 |
| 28 | Cl | Cl | $OCH_2$—$CH(CH_3)$—$CH_3$ | 2',4',6'-Br | 3 | H | 136–39 |
| 29 | Br | Br | $OCH_3$ | 2',6'-$CH_3$ | 2 | H | 161 |
| 30 | Br | Br | $CH_3$ | 2'-Cl | 1 | 5'-$CF_3$ | 176–78 |
| 31 | Br | Br | $C_2H_5$ | 2'-Cl | 1 | 5'-$CF_3$ | 136–37 |
| 32 | Cl | Br | $CH_3$ | 2',6'-$CH_3$ | 2 | H | 193–94 |
| 33 | Cl | Br | $OCH_3$ | 2',5'-$CH_3$ | 2 | H | 158 |
| 34 | Cl | Br | $OC_2H_5$ | 2'-Cl | 1 | 5'-$CF_3$ | 98 |
| 35 | Cl | Br | $CH_3$ | 2',6'-$CH(CH_3)_2$ | 2 | H | 166 |
| 36 | Cl | Br | $C_2H_5$ | 2',6'-$CH(CH_3)_2$ | 2 | H | 155 |
| 37 | Cl | Cl | $CH_3$ | 2',6'-$CH(CH_3)_2$ | 2 | H | 169–70 |
| 38 | Cl | Cl | $C_2H_5$ | 2',6'-$CH(CH_3)_2$ | 2 | H | 155 |
| 39 | Cl | Cl | $CCH_3$ | 2',6'-$CH(CH_3)_2$ | 2 | H | 144 |
| 40 | Cl | Cl | $CH_3$ | 2',6'-$CH_3$ | 2 | H | 185–86 |
| 41 | Cl | Cl | $C_2H_5$ | 2',6'-$CH_3$ | 2 | H | 155–56 |
| 42 | Cl | Cl | $OCH_3$ | 2',6'-$CH_3$ | 2 | H | 153 |
| 43 | Cl | Cl | $CH_3$ | 2'-Cl | 1 | 5'-$CF_3$ | 152 |
| 44 | Cl | Cl | $OCH_3$ | 2'-Cl | 1 | 5'-$CF_3$ | 129 |
| 45 | Cl | Br | $CH_3$ | 2',6'-$C_2H_5$ | 2 | H | 179 |
| 46 | Cl | Br | $C_2H_5$ | 2',6'-$C_2H_5$ | 2 | H | 169 |
| 47 | Cl | Br | $C_2H_5$ | 2',6'—$CH_3$ | 2 | H | 164–66 |
| 48 | Cl | Br | $OCH_3$ | 2',6'-$CH(CH_3)_2$ | 2 | H | 135–57 |
| 49 | $C(CH_3)_3$ | Br | $CH_3$ | 3',5'-$CF_3$ | 2 | H | 211 |
| 50 | $C(CH_3)_3$ | Br | $OCH_3$ | 3',5'-$CF_3$ | 2 | H | 164 |
| 51 | $C(CH_3)_3$ | Br | $OCH_3$ | 2'-Cl | 1 | 5'-$CF_3$ | 122–23 |
| 52 | $C(CH_3)_3$ | Br | $CH_3$ | 2'-Cl | 1 | 5'-$CF_3$ | 146 |
| 53 | $C(CH_3)_3$ | Br | $CH_3$ | 2',4',6'-Br | 3 | H | 195 |
| 54 | Cl | H | $OC_2H_5$ | 2'-Cl | 1 | H | 93–95 |
| 55 | Cl | H | $OC_2H_5$ | 4'-Cl | 1 | H | 110 |
| 56 | Br | Br | $CH_3$ | 3',5'-$CF_3$ | 2 | H | 173–74 |
| 57 | H | $NO_2$ | $C_3H_7$ | 2'-Cl | 1 | 4'-$NO_2$ | 75–76 |

EXAMPLE 58

Plutella test

Solvent: 3 parts by weight dimethyl formamide
Emulsifier: 1 part by weight alkylaryl polyglycol ether To produce a suitable preparation of active compound, 1 part by weight of the active compound is mixed with the stated amount of solvent containing the stated amount of emulsifier and the concentrate is diluted with water to the desired concentration.

Cabbage leaves (*Brassica oleracea*) are sprayed with the preparation of the active compound until dew moist and are then infested with caterpillars of the diamondback moth (*Plutella maculipennis*).

After the specified periods of time, the degree of destruction is determined as a percentage: 100% means that all the caterpillars are killed whereas 0% means that none of the caterpillars are killed.

The active compounds, the concentrations of the active compounds, the evaluation time and the results can be seen from the following Table 2:

Table 2

(Plant-damaging insects)
Plutella test

| Active compounds | Concentration of active compound in % | Degree of destruction in % after 3 days |
|---|---|---|
| (A) 5-Cl, 2-OH, 3-(4-Cl-phenyl)-N-(4-chlorophenyl)benzamide (known) | 0.2<br>0.02<br>0.002<br>0.0002 | 100<br>100<br>60<br>0 |
| (B) 5-Cl, 2-OH, 3-(4-Cl-phenyl)-N-(3,4-dichlorophenyl)benzamide (known) | 0.2<br>0.02<br>0.002<br>0.0002 | 100<br>100<br>50<br>0 |
| (1) 5-Cl, 3-Br, 2-(OC(O)OCH$_3$)-N-(3,5-bis(trifluoromethyl)phenyl)benzamide | 0.2<br>0.02<br>0.002 | 100<br>100<br>95 |
| (2) 5-Cl, 3-Br, 2-(OC(O)C$_2$H$_5$)-N-(2-Cl-5-CF$_3$-phenyl)benzamide | 0.2<br>0.02<br>0.002<br>0.0002 | 100<br>100<br>100<br>85 |
| (9) 5-Cl, 3-Br, 2-(OC(O)OCH$_3$)-N-(2-Cl-5-CF$_3$-phenyl)benzamide | 0.2<br>0.02<br>0.002<br>0.002 | 100<br>100<br>100<br>65 |
| (11) 3,5-diBr, 2-(OC(O)OCH$_3$)-N-(3,5-bis(trifluoromethyl)phenyl)benzamide | 0.2<br>0.02<br>0.002 | 100<br>100<br>100 |
| (12) 3,5-diBr, 2-(OC(O)OCH$_3$)-N-(2-Cl-5-CF$_3$-phenyl)benzamide | 0.2<br>0.02<br>0.002 | 100<br>100<br>95 |

Table 2-continued

(Plant-damaging insects)
Plutella test

| Active compounds | Concentration of active compound in % | Degree of destruction in % after 3 days |
|---|---|---|
| (13) [3,5-dichloro-2-(propionyloxy)-N-(2-chloro-5-trifluoromethylphenyl)benzamide structure] | 0.2<br>0.02<br>0.002 | 100<br>100<br>100 |

EXAMPLE 59

Phaedon larvae test

Solvent: 3 parts by weight dimethyl formamide
Emulsifier: 1 part by weight alkylaryl polyglycol ether To produce a suitable preparation of active compound, 1 part by weight of the active compound is mixed with the stated amount of solvent containing the stated amount of emulsifier, and the concentrate is diluted with water to the desired concentration.

Cabbage leaves (*Brassica oleracea*) are sprayed with the preparation of the active compound until dripping wet and then infested with mustard beetle larvae (*Phaedon cochleariae*).

After the specified periods of time, the degree of destruction is determined as a percentage: 100% means that all the beetle larvae are killed. 0% means that none of the beetle larvae are killed.

The active compounds, the concentration of the active compound, the times of evaluation and the results can be seen from the following Table 3:

Table 3

(plant-damaging insects)
Phaedon larvae test

| Active compounds | Concentration of active compound in % | Degree of destruction in % after 3 days |
|---|---|---|
| (A) [5-chloro-2-hydroxy-4'-chloro-N-(4-chlorophenyl)biphenyl-3-carboxamide structure] (known) | 0.2<br>0.02 | 100<br>20 |
| (4) [3,5-dibromo-2-(acetyloxy)-N-(2,6-diisopropylphenyl)benzamide structure] | 0.2<br>0.02<br>0.002 | 100<br>100<br>100 |
| (5) [3,5-dibromo-2-(propionyloxy)-N-(2,6-diisopropylphenyl)benzamide structure] | 0.2<br>0.02<br>0.002 | 100<br>100<br>100 |
| (6) [3,5-dichloro-2-(propionyloxy)-N-(2,6-diisopropylphenyl)benzamide structure] | 0.2<br>0.02<br>0.002 | 100<br>100<br>100 |

Table 3-continued (plant-damaging insects)
Phaedon larvae test

| Active compounds | Concentration of active compound in % | Degree of destruction in % after 3 days |
| --- | --- | --- |
| (7) Cl—[benzene with C(=O)—NH—(3,5-bis-CF₃-phenyl) and O—C(=O)—CH₃ and Br substituents] | 0.2<br>0.02<br>0.002 | 100<br>100<br>100 |
| (8) Cl—[benzene with C(=O)—NH—(3,5-bis-CF₃-phenyl) and O—C(=O)—C₂H₅ and Br substituents] | 0.2<br>0.02<br>0.002 | 100<br>100<br>100 |
| (9) Cl—[benzene with C(=O)—NH—(2-Cl, 5-CF₃-phenyl) and O—C(=O)—OCH₃ and Br substituents] | 0.2<br>0.02<br>0.002<br>0.0002 | 100<br>100<br>90<br>80 |
| (10) Cl—[benzene with C(=O)—NH—(2-Cl, 5-CF₃-phenyl) and O—C(=O)—CH₃ and Br substituents] | 0.2<br>0.02<br>0.002 | 100<br>100<br>100 |

EXAMPLE 60

Tetranychus test/resistant

Solvent: 3 parts by weight dimethyl formamide
Emulsifier: 1 part by weight alkylaryl polyglycol ether To produce a suitable preparation of active compound, 1 part by weight of the active compound is mixed with the stated amount of solvent containing the stated amount of emulsifier and the concentrate so obtained is diluted with water to the desired concentration.

Bean plants (*Phaseolus vulgaris*), which have a height of approximately 10–30 cm., are sprayed with the preparation of the active compound until dripping wet. These bean plants are heavily infested with spider mites (*Tetranychus urticae*) in all stages of development.

After the specified periods of time, the effectiveness of the preparation of active compound is determined by counting the dead mites. The degree of destruction thus obtained is expressed as a percentage: 100% means that all the spider mites are killed whereas 0% means that none of the spider mites are killed.

The active compounds, the concentrations of the active compounds, the evaluation times and the results can be seen from the following Table 4:

Table 4

(plant-damaging mites)
Tetranychus test

| Active compounds | Concentration of active compound in % | Degree of destruction in % after 2 days |
| --- | --- | --- |
| (A) Cl—[benzene with C(=O)—NH—(4-Cl-phenyl), OH, and 4-Cl-phenyl substituents] (known) | 0.2 | 0 |

Table 4-continued

(plant-damaging mites)
Tetranychus test

| Active compounds | Concentration of active compound in % | Degree of destruction in % after 2 days |
|---|---|---|
| (B) [known compound: 5-chloro-2-hydroxy-4'-chloro-biphenyl-3-carboxylic acid 2,4,5-trichloroanilide] | 0.2 | 0 |
| (14) 3,5-dibromo-2-(methoxycarbonyloxy)-benzoic acid 2,6-dimethylanilide | 0.2 | 95 |
| (15) 3-bromo-5-chloro-2-(methoxycarbonyloxy)-benzoic acid 2,6-diethylanilide | 0.2 | 80 |
| (16) 3-bromo-5-tert-butyl-2-(methoxycarbonyloxy)-benzoic acid 2,4,6-tribromoanilide | 0.2 | 90 |
| (17) 3,5-dichloro-2-(methoxycarbonyloxy)-benzoic acid 2,4,6-tribromoanilide | 0.2 / 0.02 | 100 / 40 |
| (18) 3,5-dichloro-2-(ethoxycarbonyloxy)-benzoic acid 3-chloroanilide | 0.2 | 98 |
| (19) 3,5-dichloro-2-(ethoxycarbonyloxy)-benzoic acid 4-chloroanilide | 0.2 | 100 |
| (20) 3,5-dichloro-2-(ethoxycarbonyloxy)-benzoic acid 2,5-dichloroanilide | 0.2 / 0.02 | 100 / 90 |

Table 4-continued (plant-damaging mites)
Tetranychus test

| | Active compounds | Concentration of active compound in % | Degree of destruction in % after 2 days |
|---|---|---|---|
| (21) | 3,5-dichloro-2-(ethoxycarbonyloxy)-N-(2,5-dichloro-4-methylthiophenyl)benzamide | 0.2 | 80 |
| (22) | 3,5-dibromo-2-(ethoxycarbonyloxy)-N-(4-bromophenyl)benzamide | 0.2 | 99 |
| (23) | 3,5-dibromo-2-(ethoxycarbonyloxy)-N-(2,3-dichlorophenyl)benzamide | 0.2 | 80 |
| (24) | 3-nitro-2-(ethoxycarbonyloxy)-N-(4-chlorophenyl)benzamide | 0.2 | 90 |
| (25) | 3,5-dichloro-2-(ethoxycarbonyloxy)-N-(2,3,5-trichloro-6-(ethoxycarbonyloxy)phenyl)benzamide | 0.2 | 80 |
| (26) | 3,5-dibromo-2-(butoxycarbonyloxy)-N-(2,4-dichlorophenyl)benzamide | 0.2 / 0.02 | 95 / 90 |
| (27) | 3,5-dibromo-2-(isobutoxycarbonyloxy)-N-(2,4-dichlorophenyl)benzamide | 0.2 | 98 |
| (28) | 3,5-dichloro-2-(isobutoxycarbonyloxy)-N-(2,4-dibromophenyl)benzamide | 0.2 | 99 |

It will be appreciated that the instant specification and examples are set forth by way of illustration and not limitation, and that various modifications and changes may be made without departing from the spirit and scope of the present invention.

What is claimed is:

1. A compound selected from the group consisting of 3-bromo-2′,5-dichloro-5′-trifluromethyl-2-propionoxy-benzoic acid anilide and 3,5-dibromo-2′,6′-di-isopropyl-2-acetoxy-benzoic acid anilide.

2. A compound according to claim 1, wherein such compound is 3-bromo-2′,5-dichloro-5′-trifluoromethyl-2-propionoxy-benzoic acid anilide of the formula 3. A compound according to claim 1, wherein such compound is 3,5-dibromo-2',6'-di-isopropyl-2-acetoxybenzoic acid anilide of the formula

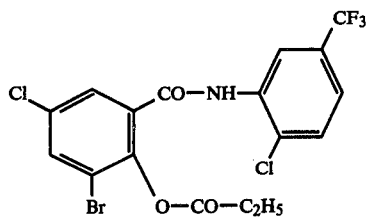

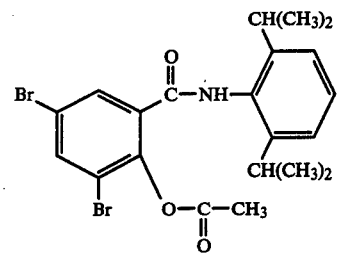

4. A method of combating insect or acarid pests which comprises applying to the pests or to a habitat thereof a compound according to claim 1 alone or in the form of a composition containing it as active ingredient in admixture with a diluent or carrier.

* * * * *